United States Patent [19]

Wenderoth et al.

[11] Patent Number: 5,057,537

[45] Date of Patent: Oct. 15, 1991

[54] ORTHO-SUBSTITUTED 1-NAPHTHYL ETHERS AND FUNGICIDES CONTAINING THESE

[75] Inventors: Bernd Wenderoth, Lampertheim; Hubert Sauter, Mannheim; Albrecht Harreus, Ludwigshafen; Franz Roehl, Ludwigshafen; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 474,506

[22] Filed: Feb. 2, 1990

[30] Foreign Application Priority Data

Feb. 28, 1989 [DE] Fed. Rep. of Germany ....... 3906160

[51] Int. Cl.$^5$ .............................................. A01N 37/05
[52] U.S. Cl. ...................... 514/510; 560/10; 560/21; 560/35; 558/389
[58] Field of Search ............................ 560/35, 10, 21; 514/510; 558/384

[56]         References Cited
       U.S. PATENT DOCUMENTS 3,978,116  8/1976  Fried et al. .
4,802,913  2/1989  Clough et al. .
4,822,908  3/1989  Karbach et al. .
4,829,085  5/1989  Wenderoth et al. ............... 514/522
4,913,721  4/1990  Clough et al. .

FOREIGN PATENT DOCUMENTS 0178826   4/1986  European Pat. Off. .
0254426   1/1988  European Pat. Off. .
0336211  10/1989  European Pat. Off. .
2192883   1/1988  United Kingdom .

Primary Examiner—Bruce Gray
Attorney, Agent, or Firm—Oblon, Spivak, McClelland, Maier & Neustadt

[57]            ABSTRACT

Ortho-substituted 1-napthyl ethers of the formula

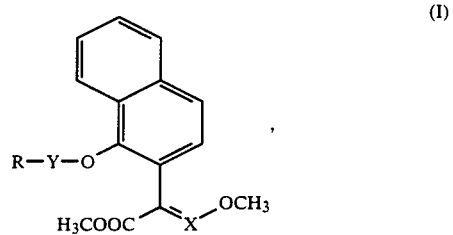

where X is CH or N, Y is saturated or unsaturated alkylene and R is aryl, aryloxy, arylthio or arylalkoxy, the aromatic ring being substituted or unsubstituted, and fungicides containing these compounds.

6 Claims, No Drawings

ORTHO-SUBSTITUTED 1-NAPHTHYL ETHERS AND FUNGICIDES CONTAINING THESE

The present invention relates to novel ortho-substituted 1-naphthyl ethers, the prepartion thereof, fungicides containing these, and the use thereof as fungicides.

The use of oxime ethers such as methyl 2-benzyloxyphenyl glyoxylate O-methyloxime as fungicides has been disclosed (EP 253213, 254426). However, their fungicidal action is often inadequate.

We have found that ortho-substituted 1-naphthyl ethers of the general formula I

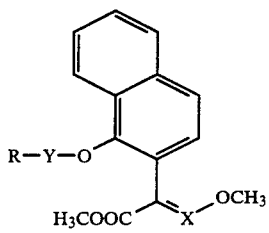
(I)

where X is CH or N, Y is $C_1$–$C_{12}$-alkylene which can be unsaturated and R is aryl, aryloxy, arylthio or arylalkoxy, it being possible for the aromatic ring to be substituted one to five times by the following: halogen, $C_1$–$C_6$-alkyl, $C_1$–$C_6$-alkoxy, $C_1$–$C_4$-alkylthio, $C_1$–$C_2$-haloalkyl, aryl, aryl-$C_1$–$C_2$-alkoxy, $C_1$–$C_4$-alkylcarbonyl, amino which is substituted once or twice by $C_1$–$C_4$-alkyl, or cyano or nitro, have an excellent fungicidal action.

Examples of possible meanings of the radicals listed for the general formula are the following:

X can be CH or N,

Y can be straight-chain $C_1$–$C_{12}$-alkylene, in particular $C_1$–$C_4$-alkylene (e.g. methylene, ethylene, propylene, butylene, pentylene, hexylene, heptylene, octylene, nonylene, decylene), branched $C_2$–$C_{12}$-alkylene (e.g. methylethylene) or $C_4$–$C_{12}$-alkenylene (e.g. butenylene), R can be aryl (phenyl), aryloxy (phenoxy, 1-naphthyloxy, 2-naphthyloxy), arylthio (phenylthio) or arylalkoxy (benzyloxy), it being possible for the aromatic ring to be substituted one to five (one to three) times by the following:

halogen (e.g. fluorine, chlorine, bromine, iodine),
$C_1$–$C_6$-alkyl (e.g. methyl, ethyl, n- or iso-propyl, n-, iso-, sec- or tert-butyl, n-, iso-, sec-, tert- or neopentyl, hexyl), $C_1$–$C_6$-alkoxy (e.g. methoxy, ethoxy, n- or iso-propoxy, n-, iso-, sec- or tert-butoxy), $C_1$–$C_4$-alkylthio (e.g. methylthio, ethylthio), $C_1$–$C_2$-haloalkyl (e.g. difluoromethyl, trifluoromethyl), aryl (e.g. phenyl), aryl-$C_1$–$C_2$-alkoxy (e.g. benzyloxy), $C_1$–$C_4$-alkylcarbonyl (e.g. acetyl), amino which is substituted once or twice by $C_1$–$C_4$-alkyl (e.g. dimethylamino), or cyano or nitro.

The novel compounds of the formula I can, because of the C=N double bond, result as E/Z isomer mixtures which can be separated in a conventional manner, e.g. by crystallization or chromatography, into the individual components. Both the individual isomers and the mixtures thereof are embraced by the invention and can be used as fungicides.

The novel compounds of the general formula I can be prepared by the following processes, for example:

starting from 1-naphthol it is possible by Friedel-Crafts acylation with methyl oxalyl chloride in a suitable solvent (for example dichloromethane) in the presence of a Lewis acid (for example titanium tetrachloride) to synthesize the α-keto ester III which is known from the literature (O. Piccolo et al., Tetrahedron 42 (1986), 885–891).

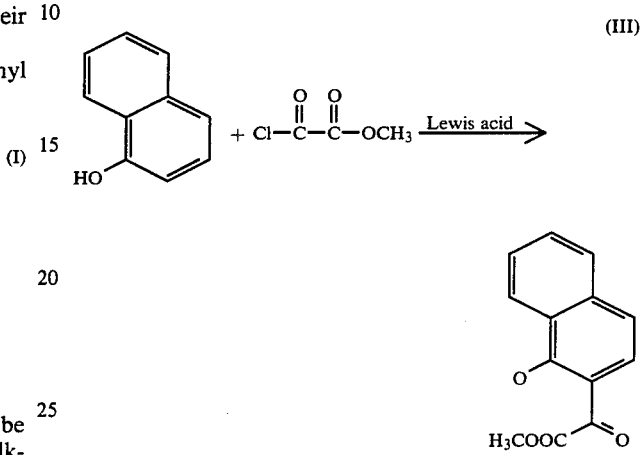
(III)

Starting from the compound of the formula III it is possible to obtain the novel and valuable intermediates of the formula IV which are likewise embraced by this invention and in which X is CH or N

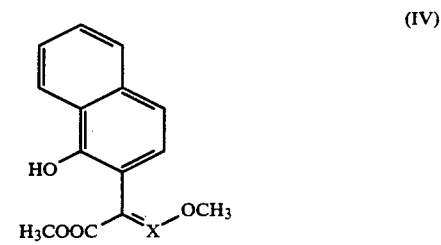
(IV)

The α-keto ester III can be converted into the novel oxime ether derivative of the formula IV (X=N) by reacting it with O-methylhydroxylamine, or by reacting first with hydroxylamine to give the corresponding oxime and then with a methylating agent such as methyl iodide or dimethyl sulfate (cf. EP 253213).

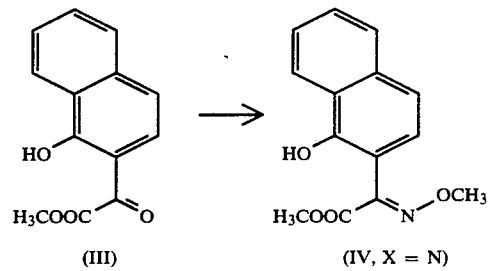

(III)               (IV, X = N)

The α-keto ester III can be converted into the novel enol ether derivative of the formula IV (X=CH) by subjecting it to a Wittig reaction with methoxymethyltriphenylphosphonium halide (cf. EP 44448).

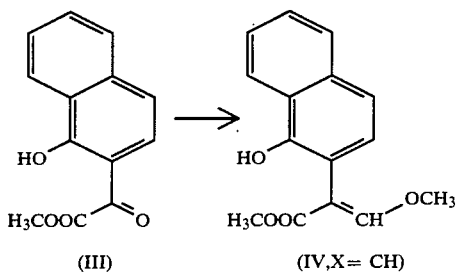

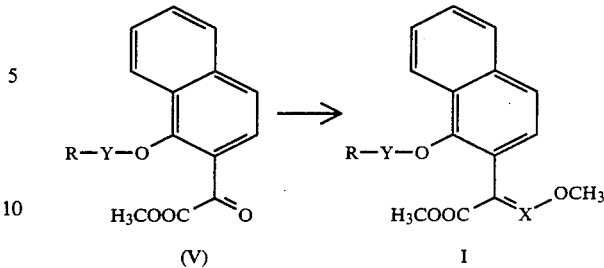

The novel compounds of the general formula I can be prepared, for example, by reacting the compound of the general formula IV with halides of the formula II in a suitable solvent such as methanol or N,N-dimethylformamide by conventional processes (cf. Houben-Weyl, Methoden der organischen Chemie, volume 6/3, p. 54, Thieme-Verlag, Stuttgart 1965).

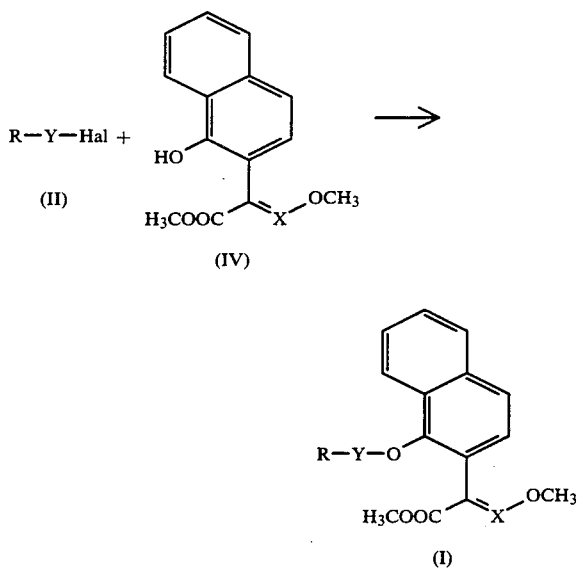

R, Y and X have the abovementioned meanings. Hal is Cl, Br or I.

The novel compounds of the general formula I can also be prepared, for example, by reacting the α-keto ester of the formula III with halides of the formula II in a suitable solvent such as methanol or N,N-dimethylformamide by conventional processes (cf. Houben-Weyl, Methoden der organischen Chemie, volume 6/3, p. 54, Thieme-Verlag, Stuttgart 1965) to give the novel α-keto carboxylic esters of the formula V:

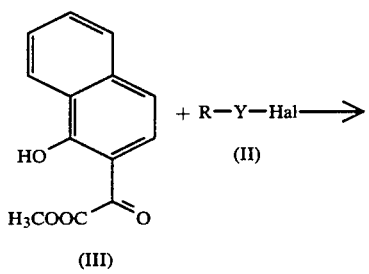

These esters of the general formula V can be converted into the compounds of the general formula I according to the invention; reaction with O-methylhydroxylamine or with hydroxylamine and subsequent methylation with a methylating agent such as methyl iodide or dimethyl sulfate result in the novel oxime ether derivatives of the formula I (X=N) (cf. EP 253213), and a Wittig reaction with methoxymethyltriphenylphosphonium halide results in the novel enol ether derivatives of the formula I (X=CH) (cf. EP 44448).

The α-keto carboxylic esters of the formula V are novel and valuable intermediates and are likewise embraced by this invention.

The preparation of the novel compounds of the formulae I and IV is illustrated by the following examples:

Preparation Examples a) 28.5 g (0.15 mol) of titanium tetrachloride are added under nitrogen at −10° C. to 150 ml of methylene chloride. This is followed by dropwise addition at −40° C. of, firstly, 22.3 g (0.15 mol) of 1-naphthol dissolved in 100 ml of methylene chloride and then 18.5 g (0.15 mol) of methyl oxalyl chloride. After stirring at this temperature for 30 min, a little dilute hydrochloric acid is added at room temperature (20° C.), and the mixture is poured onto ice. The organic phase is washed 1× with $H_2O$, dried over sodium sulfate and concentrated. 30 g (0.13 mol) of methyl 1-hydroxy-2-naphthylglyoxylate (87% yield) are obtained.

$^1$H NMR (CDCl$_3$): δ=4.05 (s, 3H), 7.25 (d, 1H), 7.40–7.80 (m, 4H), 8.45 (d, 1H), 13.00 (s, 1H).

b) 69 g (0.26 mol) of methyl 1-hydroxy-2-naphthylglyoxylate and 44 g (0.53 mol) of O-methylhydroxylamine hydrochloride in 800 ml of methanol are stirred under reflux for 6 h. The mixture is then concentrated; the residue is taken up in ethyl acetate, and the solution is washed with $H_2O$, dried over sodium sulfate and concentrated again. 52 g (0.20 mol) of methyl 1-hydroxy-2-naphthylglyoxylate O-methyloxime (77% yield) are obtained.

$^1$H NMR (CDCl$_3$): δ=4.00 (s, 3H), 4.05 (s, 3H), 7.00 (d, 1H), 7.30 (d, 1H), 7.40–7.90 (m, 4H), 8.35 (m, 1H), 10.90 (s, 1H).

c) 5 g (19 mmol) of methyl 1-hydroxy-2-naphthylglyoxylate O-methyloxime, 2.7 g (19 mmol) of 2-fluorobenzyl chloride and 2.6 g (19 mmol) of potassium carbonate in 65 ml of methanol are stirred under reflux for 8 h. The mixture is cooled to room temperature and the solids are removed by filtration. The filtrate is concentrated, and dilute sodium hydroxide solution is added. The mixture is then extracted by shaking several times with ether; the combined ether phases are washed with $H_2O$, dried over sodium sulfate and concentrated. 5 g (13.6 mmol) of methyl 1-(2-fluorobenzyloxy)-2-naphthylglyoxylate O-methyloxime (yield 71%) are obtained (compound no. 2, Table 1).

$^1$H NMR (CDCl$_3$): δ=3.65 (s, 3H), 4.10 (s, 3H), 5.10 (s, 2H), 7.00–8.20 (m, 10H).

The following compounds are prepared in a corresponding manner.

TABLE 1

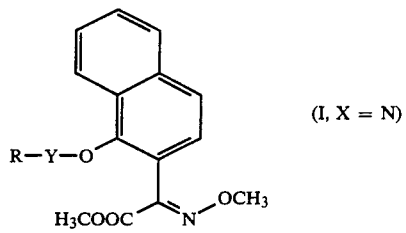

(I, X = N)

| Comp. no. | R | Y | mp (°C.) | IR (cm$^{-1}$) |
|---|---|---|---|---|
| 1 | C$_6$H$_5$ | —CH$_2$— | resin | 2930, 1743, 1358, 1227, 1061, 1036, 752 |
| 2 | 2-F—C$_6$H$_4$ | —CH$_2$— | oil | 2940, 1743, 1493, 1231, 1037, 757 |
| 3 | 3-F—C$_6$H$_4$ | —CH$_2$— | resin | 2950, 1743, 1358, 1263, 1037, 752 |
| 4 | 4-F—C$_6$H$_4$ | —CH$_2$— | resin | 2940, 1742, 1511, 1225, 1037, 821 |
| 5 | 2,4-F$_2$—C$_6$H$_3$ | —CH$_2$— | resin | 2940, 1742, 1506, 1227, 1101, 1037, 852 |
| 6 | 2-Cl—C$_6$H$_4$ | —CH$_2$— | resin | 2940, 1743, 1358, 1226, 1037, 753 |
| 7 | 3-Cl—C$_6$H$_4$ | —CH$_2$— | resin | 2940, 1742, 1356, 1226, 1037, 752 |
| 8 | 4-Cl—C$_6$H$_4$ | —CH$_2$— | resin | 2940, 1743, 1357, 1227, 1037, 810 |
| 9 | 2,4-Cl$_2$—C$_6$H$_3$ | —CH$_2$— | 95 | 2940, 1733, 1474, 1231, 1098, 1037, 815 |
| 10 | 2,6-Cl$_2$—C$_6$H$_3$ | —CH$_2$— | | |
| 11 | 3,5-Cl$_2$—C$_6$H$_3$ | —CH$_2$— | | |
| 12 | 2,4,6-Cl$_3$—C$_6$H$_2$ | —CH$_2$— | | |
| 13 | 2-Br—C$_6$H$_4$ | —CH$_2$— | resin | 2940, 1743, 1356, 1226, 1037, 752 |
| 14 | 3-Br—C$_6$H$_4$ | —CH$_2$— | resin | 2940, 1742, 1355, 1226, 1061, 1036 |
| 15 | 4-Br—C$_6$H$_4$ | —CH$_2$— | resin | 2940, 1742, 1356, 1227, 1037, 808 |
| 16 | 2,4-Br$_2$—C$_6$H$_3$ | —CH$_2$— | | |
| 17 | 2-J-C$_6$H$_4$ | —CH$_2$— | resin | 2945, 1743, 1335, 1225, 1100, 1062, 1037, 750 |
| 18 | 2-CH$_3$—C$_6$H$_4$ | —CH$_2$— | resin | 2930, 1742, 1359, 1226, 1036, 748 |
| 19 | 3-CH$_3$—C$_6$H$_4$ | —CH$_2$— | resin | 2940, 1743, 1355, 1226, 1037, 752 |
| 20 | 4-CH$_3$—C$_6$H$_4$ | —CH$_2$— | resin | 2930, 1743, 1358, 1225, 1060, 1037 |
| 21 | 2,4-(CH$_3$)$_2$—C$_6$H$_3$ | —CH$_2$— | | |
| 22 | 2,5-(CH$_3$)$_2$—C$_6$H$_3$ | —CH$_2$— | resin | 2920, 1742, 1358, 1225, 1100, 1061, 1036, 818 |
| 23 | 2,4,6-(CH$_3$)$_3$—C$_6$H$_2$ | —CH$_2$— | | |
| 24 | 4-t-C$_4$H$_9$—C$_6$H$_4$ | —CH$_2$— | resin | 2962, 1745, 1356, 1226, 1100, 1061, 1037, 817 |
| 25 | 4-i-C$_3$H$_7$—C$_6$H$_4$ | —CH$_2$— | | |
| 26 | 4-C$_2$H$_5$—C$_6$H$_4$ | —CH$_2$— | resin | 2950, 1743, 1358, 1225, 1061, 1037, 819, 752 |
| 27 | 2-CH$_3$O—C$_6$H$_4$ | —CH$_2$— | | |
| 28 | 3-CH$_3$O—C$_6$H$_4$ | —CH$_2$— | resin | 2930, 1742, 1357, 1265, 1227, 1037 |
| 29 | 4-CH$_3$O—C$_6$H$_4$ | —CH$_2$— | | |
| 30 | 4-C$_2$H$_5$O—C$_6$H$_4$ | —CH$_2$— | | |
| 31 | 4-i-C$_3$H$_7$O—C$_6$H$_4$ | —CH$_2$— | | |
| 32 | 2-CF$_3$—C$_6$H$_4$ | —CH$_2$— | | |
| 33 | 3-CF$_3$—C$_6$H$_4$ | —CH$_2$— | resin | 1940, 1743, 1331, 1166, 1126, 1037 |
| 34 | 4-CF$_3$—C$_6$H$_4$ | —CH$_2$— | | |
| 35 | 2-CN—C$_6$H$_4$ | —CH$_2$— | 81–85 | 2940, 2230, 1742, 1360, 1228, 1036, 764 |
| 36 | 3-CN—C$_6$H$_4$ | —CH$_2$— | resin | 2940, 2225, 1741, 1358, 1229, 1036, 796 |
| 37 | 4-CN—C$_6$H$_4$ | —CH$_2$— | resin | 2930, 2220, 1741, 1359, 1228, 1036, 819 |
| 38 | 2-NO$_2$—C$_6$H$_4$ | —CH$_2$— | | |
| 39 | 3-NO$_2$—C$_6$H$_4$ | —CH$_2$— | resin | 2940, 1737, 1531, 1350, 1229, 1038, 730 |
| 40 | 4-NO$_2$—C$_6$H$_4$ | —CH$_2$— | | |
| 41 | 3-C$_6$H$_5$—C$_6$H$_4$ | —CH$_2$— | | |
| 42 | 4-C$_6$H$_5$—C$_6$H$_4$ | —CH$_2$— | | |
| 43 | 4-C$_6$H$_5$O—C$_6$H$_4$ | —CH$_2$— | | |
| 44 | 2-F, 3-CH$_3$—C$_6$H$_3$ | —CH$_2$— | | |
| 45 | 2-Cl, 3-CH$_3$—C$_6$H$_3$ | —CH$_2$— | resin | 2940, 1743, 1354, 1225, 1102, 1063, 1037, 772 |
| 46 | 2-Br, 3-CH$_3$—C$_6$H$_3$ | —CH$_2$— | 109 | 2935, 1738, 1353, 1225, 1102, 1062, 1032, 772 |
| 47 | 2-Cl, 3-i-C$_3$H$_7$—C$_6$H$_3$ | —CH$_2$— | resin | 2964, 1744, 1355, 1225, 1102, 1063, 1037, 756 |
| 48 | 2-CH$_3$, 3-i-C$_3$H$_7$—C$_6$H$_3$ | —CH$_2$— | | |
| 49 | 2-CH$_3$, 3-C$_6$H$_5$—C$_6$H$_3$ | —CH$_2$— | | |
| 50 | 2-Cl, 3-C$_6$H$_5$—C$_6$H$_3$ | —CH$_2$— | | |
| 51 | 2-CH$_3$O, 3-i-C$_3$H$_7$—C$_6$H$_3$ | —CH$_2$— | | |
| 52 | 2,4,5-Cl$_3$—C$_6$H$_2$ | —CH$_2$— | | |
| 53 | 2,4,5-(CH$_3$)$_3$—C$_6$H$_2$ | —CH$_2$— | | |
| 54 | 2-CH$_3$O, 5-NO$_2$—C$_6$H$_3$ | —CH$_2$— | | |
| 55 | 2,5-Cl$_2$—C$_6$H$_3$ | —CH$_2$— | | |
| 56 | 2,5-F$_2$—C$_6$H$_3$ | —CH$_2$— | | |
| 57 | 2-Cl, 5-CH$_3$—C$_6$H$_3$ | —CH$_2$— | | |
| 58 | 2-F, 3-CH$_3$—C$_6$H$_3$ | —CH$_2$— | | |
| 59 | 2,3-F$_2$—C$_6$H$_3$ | —CH$_2$— | | |
| 60 | 2,3-Cl$_2$—C$_6$H$_3$ | —CH$_2$— | | |
| 61 | 2-F, 3-Cl—C$_6$H$_3$ | —CH$_2$— | | |
| 62 | 2-F, 4-Br—C$_6$H$_3$ | —CH$_2$— | | |
| 63 | 2,6-F$_2$—C$_6$H$_3$ | —CH$_2$— | | |

TABLE 1-continued

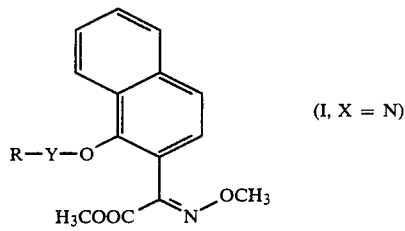

(I, X = N)

| Comp. no. | R | Y | mp (°C.) | IR (cm$^{-1}$) |
|---|---|---|---|---|
| 64 | 2-F, 6-Cl—C$_6$H$_3$ | —CH$_2$— | | |
| 65 | 2-Cl, 6-CF$_3$—C$_6$H$_3$ | —CH$_2$— | | |
| 66 | 2,3,4,5,6-(CH$_3$)$_5$—C$_6$ | —CH$_2$— | | |
| 67 | 2,3,4,5,6-F$_5$—C$_6$ | —CH$_2$— | | |
| 68 | 2-CH$_3$, 4-Cl—C$_6$H$_3$ | —CH$_2$— | | |
| 69 | 2-Cl, 4-CH$_3$—C$_6$H$_3$ | —CH$_2$— | | |
| 70 | 2-CH$_3$O, 4-CH$_3$—C$_6$H$_3$ | —CH$_2$— | | |
| 71 | 4-CH$_3$O, 2-CH$_3$—C$_6$H$_3$ | —CH$_2$— | | |
| 72 | C$_6$H$_5$—O— | —CH$_2$—CH$_2$— | | |
| 73 | 2-F—C$_6$H$_4$—O— | —CH$_2$—CH$_2$— | | |
| 74 | 3-F—C$_6$H$_4$—O— | —CH$_2$—CH$_2$— | | |
| 75 | 4-F—C$_6$H$_4$—O— | —CH$_2$—CH$_2$— | | |
| 76 | 2-Cl—C$_6$H$_4$—O— | —CH$_2$—CH$_2$— | | |
| 77 | 3-Cl—C$_6$H$_4$—O— | —CH$_2$—CH$_2$— | | |
| 78 | 4-Cl—C$_6$H$_4$—O— | —CH$_2$—CH$_2$— | | |
| 79 | 2-CH$_3$—C$_6$H$_4$—O— | —CH$_2$—CH$_2$— | | |
| 80 | 3-CH$_3$—C$_6$H$_4$—O— | —CH$_2$—CH$_2$— | | |
| 81 | 4-CH$_3$—C$_6$H$_4$—O— | —CH$_2$—CH$_2$— | | |
| 82 | 2-CH$_3$O—C$_6$H$_4$—O— | —CH$_2$—CH$_2$— | | |
| 83 | 3-CH$_3$O—C$_6$H$_4$—O— | —CH$_2$—CH$_2$— | | |
| 84 | 4-CH$_3$O—C$_6$H$_4$—O— | —CH$_2$—CH$_2$— | | |
| 85 | 4-t-C$_4$H$_9$—C$_6$H$_4$—O— | —CH$_2$—CH$_2$— | | |
| 86 | 4-C$_2$H$_5$O—C$_6$H$_4$—O— | —CH$_2$—CH$_2$— | | |
| 87 | 4-CF$_3$—C$_6$H$_4$—O— | —CH$_2$—CH$_2$— | | |
| 88 | 4-C$_6$H$_5$—C$_6$H$_4$—O— | —CH$_2$—CH$_2$— | | |
| 89 | 4-(C$_6$H$_5$—CH$_2$—O)—C$_6$H$_4$—O— | —CH$_2$—CH$_2$— | | |
| 90 | 2,4,6-Cl$_3$—C$_6$H$_2$—O— | —CH$_2$—CH$_2$— | | |
| 91 | 2,4,6-(CH$_3$)$_3$—C$_6$H$_2$—O— | —CH$_2$—CH$_2$— | | |
| 92 | 1-naphthyl-O— | —CH$_2$—CH$_2$— | | |
| 93 | 2-naphthyl-O— | —CH$_2$—CH$_2$— | | |
| 94 | 2-Br—C$_6$H$_4$—O— | —CH$_2$—CH$_2$— | | |
| 95 | 3-Br—C$_6$H$_4$—O— | —CH$_2$—CH$_2$— | | |
| 96 | 4-Br—C$_6$H$_4$—O— | —CH$_2$—CH$_2$— | | |
| 97 | 2-CF$_3$—C$_6$H$_4$—O— | —CH$_2$—CH$_2$— | | |
| 98 | 3-CF$_3$—C$_6$H$_4$—O— | —CH$_2$—CH$_2$— | | |
| 99 | 4-CN—C$_6$H$_4$—O— | —CH$_2$—CH$_2$— | | |
| 100 | 4-CH$_3$CO—C$_6$H$_4$—O— | —CH$_2$—CH$_2$— | | |
| 101 | 3-(CH$_3$)$_2$N—C$_6$H$_4$—O— | —CH$_2$—CH$_2$— | | |
| 102 | 4-CH$_3$S—C$_6$H$_4$—O— | —CH$_2$—CH$_2$— | | |
| 103 | 2-C$_2$H$_5$O—C$_6$H$_4$—O— | —CH$_2$—CH$_2$— | | |
| 104 | 4-t-C$_4$H$_9$—C$_6$H$_4$—O— | —CH$_2$—CH$_2$— | | |
| 105 | 2,4-Cl$_2$—H$_6$H$_3$—O— | —CH$_2$—CH$_2$— | | |
| 106 | 3,4-Cl$_2$—C$_6$H$_3$—O— | —CH$_2$—CH$_2$— | | |
| 107 | 2,5-Cl$_2$—C$_6$H$_3$—O— | —CH$_2$—CH$_2$— | | |
| 108 | 2,6-Cl$_2$—C$_6$H$_3$—O— | —CH$_2$—CH$_2$— | | |
| 109 | 2,4,5-Cl$_3$—C$_6$H$_2$—O— | —CH$_2$—CH$_2$— | | |
| 110 | 2-Cl, 4-F—C$_6$H$_3$—O— | —CH$_2$—CH$_2$— | | |
| 111 | 2-Cl, 4-Br—C$_6$H$_3$—O— | —CH$_2$—CH$_2$— | | |
| 112 | 2,4-(CH$_3$)$_2$—C$_6$H$_3$—O— | —CH$_2$—CH$_2$— | | |
| 113 | 2-CH$_3$, 4-t-C$_4$H$_9$—C$_6$H$_3$—O | —CH$_2$—CH$_2$— | | |
| 114 | 2-CH$_3$, 4-Cl—C$_6$H$_3$—O— | —CH$_2$—CH$_2$— | | |
| 115 | 2-CH$_3$, 4,6-Cl$_2$—C$_6$H$_2$—O— | —CH$_2$—CH$_2$— | | |
| 116 | 2,6-(CH$_3$)$_2$—C$_6$H$_3$—O— | —CH$_2$—CH$_2$— | | |
| 117 | 2,5,6-(CH$_3$)$_3$—C$_6$H$_2$—O— | —CH$_2$—CH$_2$— | | |
| 118 | 2,4,5-(CH$_3$)$_3$—C$_6$H$_2$—O— | —CH$_2$—CH$_2$— | | |
| 119 | 2-i-C$_3$H$_7$, 5-CH$_3$—C$_6$H$_3$—O— | —CH$_2$—CH$_2$— | | |
| 120 | 3,5-(C$_2$H$_5$)$_2$—C$_6$H$_3$—O— | —CH$_2$—CH$_2$— | | |
| 121 | 2,4,6-(sec-C$_4$H$_9$)$_3$—C$_6$H$_2$—O— | —CH$_2$—CH$_2$— | | |
| 122 | 3,5-(CH$_3$O)$_2$—C$_6$H$_3$—O— | —CH$_2$—CH$_2$— | | |
| 123 | 2-CH$_3$O, 4-CH$_3$—C$_6$H$_3$—O— | —CH$_2$—CH$_2$— | | |
| 124 | 2,6-(CH$_3$)$_2$, 4-CH$_3$S—C$_6$H$_2$—O— | —CH$_2$—CH$_2$— | | |
| 125 | 2-Cl, 5-CH$_3$O—C$_6$H$_3$—O— | —CH$_2$—CH$_2$— | | |
| 126 | 2-CH$_3$, 4-CH$_3$S—C$_6$H$_3$—O— | —CH$_2$—CH$_2$— | | |
| 127 | 2,6-(CH$_3$O)$_2$—C$_6$H$_3$—O— | —CH$_2$—CH$_2$— | | |
| 128 | 2-Cl, 4-C$_6$H$_5$—C$_6$H$_3$—O— | —CH$_2$—CH$_2$— | | |
| 129 | 2,Cl, 4-CH$_3$—C$_6$H$_3$—O— | —CH$_2$—CH$_2$— | | |
| 130 | 2-CH$_3$, 6-i-C$_3$H$_7$—C$_6$H$_3$—O— | —CH$_2$—CH$_2$— | | |
| 131 | 3-t-C$_4$H$_9$, 4-CH$_3$O—C$_6$H$_3$—O— | —CH$_2$—CH$_2$— | | |

TABLE 1-continued

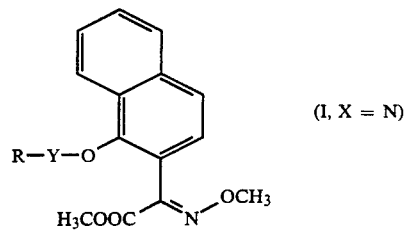

(I, X = N)

| Comp. no. | R | Y | mp (°C.) | IR (cm$^{-1}$) |
|---|---|---|---|---|
| 132 | 2,4-(CH$_3$)$_2$-1-naphthyl-O— | —CH$_2$—CH$_2$— | | |
| 133 | C$_6$H$_5$—S | —CH$_2$—CH$_2$— | | |
| 134 | 4-Cl—C$_6$H$_4$—S | —CH$_2$—CH$_2$— | | |
| 135 | 2,4,6-Cl$_3$—C$_6$H$_2$—O— | —CH$_2$—CH(CH$_3$)— | | |
| 136 | C$_6$H$_5$—O— | —CH$_2$—CH(CH$_3$)— | | |
| 137 | C$_6$H$_5$—O— | —(CH$_2$)$_3$— | | |
| 138 | 2-F—C$_6$H$_4$—O— | —(CH$_2$)$_3$— | | |
| 139 | 3-F—C$_6$H$_4$—O— | —(CH$_2$)$_3$— | | |
| 140 | 4-F—C$_6$H$_4$—O— | —(CH$_2$)$_3$— | | |
| 141 | 2-Cl—C$_6$H$_4$—O— | —(CH$_2$)$_3$— | | |
| 142 | 3-Cl—C$_6$H$_4$—O— | —(CH$_2$)$_3$— | | |
| 143 | 4-Cl—C$_6$H$_4$—O— | —(CH$_2$)$_3$— | | |
| 144 | 2-CH$_3$—C$_6$H$_4$—O— | —(CH$_2$)$_3$— | | |
| 145 | 3-CH$_3$—C$_6$H$_4$—O— | —(CH$_2$)$_3$— | | |
| 146 | 4-CH$_3$—C$_6$H$_4$—O— | —(CH$_2$)$_3$— | | |
| 147 | 2-CH$_3$O—C$_6$H$_4$—O— | —(CH$_2$)$_3$— | | |
| 148 | 3-CH$_3$O—C$_6$H$_4$—O— | —(CH$_2$)$_3$— | | |
| 149 | 4-CH$_3$O—C$_6$H$_4$—O— | —(CH$_2$)$_3$— | | |
| 150 | 4-t-C$_4$H$_9$—C$_6$H$_4$—O— | —(CH$_2$)$_3$— | | |
| 151 | 4-C$_2$H$_5$O—C$_6$H$_4$—O— | —(CH$_2$)$_3$— | | |
| 152 | 4-CF$_3$—C$_6$H$_4$—O— | —(CH$_2$)$_3$— | | |
| 153 | 4-C$_6$H$_5$—C$_6$H$_4$—O— | —(CH$_2$)$_3$— | | |
| 154 | 4-(C$_6$H$_5$—CH$_2$—O)—C$_6$H$_4$—O— | —(CH$_2$)$_3$— | | |
| 155 | 2,4,6-Cl$_3$—C$_6$H$_2$—O— | —(CH$_2$)$_3$— | | |
| 156 | 2,4,6-(CH$_3$)$_3$—C$_6$H$_2$—O— | —(CH$_2$)$_3$— | | |
| 157 | 1-naphthyl-O— | —(CH$_2$)$_3$— | | |
| 158 | 2-naphthyl-O— | —(CH$_2$)$_3$— | | |
| 159 | 2,4-Cl$_2$—C$_6$H$_3$—O— | —(CH$_2$)$_3$— | | |
| 160 | 3,5-Cl$_2$—C$_6$H$_3$—O— | —(CH$_2$)$_3$— | | |
| 161 | 3,4-Cl$_2$—C$_6$H$_3$—O— | —(CH$_2$)$_3$— | | |
| 162 | 2,6-(CH$_3$)$_2$—C$_6$H$_3$—O— | —(CH$_2$)$_3$— | | |
| 163 | 2,4-(CH$_3$)$_2$—C$_6$H$_3$—O— | —(CH$_3$)$_3$— | | |
| 164 | 3-CF$_3$—C$_6$H$_4$—O— | —(CH$_2$)$_3$— | | |
| 165 | 2-Cl, 4-CH$_3$—C$_6$H$_3$—O— | —(CH$_2$)$_3$— | | |
| 166 | C$_6$H$_5$—S | —(CH$_2$)$_3$— | | |
| 167 | C$_6$H$_5$—CH$_2$—O— | —(CH$_2$)$_3$— | | |
| 168 | C$_6$H$_5$—O— | —(CH$_2$)$_4$— | | |
| 169 | 2-F—C$_6$H$_4$—O— | —(CH$_2$)$_4$— | | |
| 170 | 3-F—C$_6$H$_4$—O— | —(CH$_2$)$_4$— | | |
| 171 | 4-F—C$_6$H$_4$—O— | —(CH$_2$)$_4$— | | |
| 172 | 2-CH$_3$—C$_6$H$_4$—O— | —(CH$_2$)$_4$— | | |
| 173 | 3-CH$_3$—C$_6$H$_4$—O— | —(CH$_2$)$_4$— | | |
| 174 | 4-CH$_3$—C$_6$H$_4$—O— | —(CH$_2$)$_4$— | | |
| 175 | 2-CH$_3$O—C$_6$H$_4$—O— | —(CH$_2$)$_4$— | | |
| 176 | 3-CH$_3$O—C$_6$H$_4$—O— | —(CH$_2$)$_4$— | | |
| 177 | 4-CH$_3$O—C$_6$H$_4$—O— | —(CH$_2$)$_4$— | | |
| 178 | 4-t-C$_4$H$_9$—C$_6$H$_4$—O— | —(CH$_2$)$_4$— | | |
| 179 | 4-C$_2$H$_5$O—C$_6$H$_4$—O— | —(CH$_2$)$_4$— | | |
| 180 | 4-CF$_3$—C$_6$H$_4$—O— | —(CH$_2$)$_4$— | | |
| 181 | 4-C$_6$H$_5$—C$_6$H$_4$—O— | —(CH$_2$)$_4$— | | |
| 182 | 4-(C$_6$H$_5$—CH$_2$—O)—C$_6$H$_4$— | —(CH$_2$)$_4$— | | |
| 183 | 2,4,6-Cl$_3$—C$_6$H$_2$—O— | —(CH$_2$)$_4$— | | |
| 184 | 2,4,6-(CH$_3$)$_3$—C$_6$H$_2$—O— | —(CH$_2$)$_4$— | | |
| 185 | 1-naphthyl-O— | —(CH$_2$)$_4$— | | |
| 186 | 2-naphthyl-O— | —(CH$_2$)$_4$— | | |
| 187 | 3-CF$_3$—C$_6$H$_4$—O— | —(CH$_2$)$_4$— | | |
| 188 | 3-iso-C$_3$H$_7$—C$_6$H$_4$—O— | —(CH$_2$)$_4$— | | |
| 189 | 4-iso-C$_3$H$_7$—C$_6$H$_4$—O— | —(CH$_2$)$_4$— | | |
| 190 | 3-t-C$_4$H$_9$—C$_6$H$_4$—O— | —(CH$_2$)$_4$— | | |
| 191 | 4-t-C$_4$H$_9$—C$_6$H$_4$—O— | —(CH$_2$)$_4$— | | |
| 192 | 3-C$_6$H$_5$—C$_6$H$_4$—O— | —(CH$_2$)$_4$— | | |
| 193 | 2,4-Cl$_2$—C$_6$H$_3$—O— | —(CH$_2$)$_4$— | | |
| 194 | 3,4-Cl$_2$—C$_6$H$_3$—O— | —(CH$_2$)$_4$— | | |
| 195 | 3,5-Cl$_2$—C$_6$H$_3$—O— | —(CH$_2$)$_4$— | | |
| 196 | 2,6-Cl$_2$—C$_6$H$_3$—O— | —(CH$_2$)$_4$— | | |
| 197 | 2-Cl, 4-CH$_3$—C$_6$H$_3$—O— | —(CH$_2$)$_4$— | | |
| 198 | 2,6-(CH$_3$)$_2$—C$_6$H$_3$—O— | —(CH$_2$)$_4$— | | |
| 199 | 2,5-(CH$_3$)$_2$—C$_6$H$_3$—O— | —(CH$_2$)$_4$— | | |

TABLE 1-continued

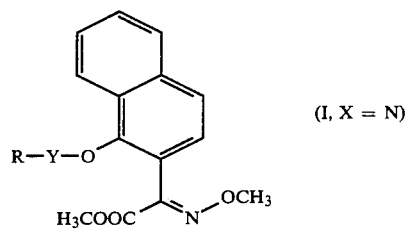

(I, X = N)

| Comp. no. | R | Y | mp (°C.) | IR (cm$^{-1}$) |
|---|---|---|---|---|
| 200 | 4-CN—C$_6$H$_4$—O— | —(CH$_2$)$_4$— | | |
| 201 | C$_6$H$_5$—S— | —(CH$_2$)$_4$— | | |
| 202 | C$_6$H$_5$—CH$_2$—O— | —(CH$_2$)$_4$— | | |
| 203 | C$_6$H$_5$—O— | —CH$_2$—CH=CH—CH$_2$— | | |
| 204 | 2-F—C$_6$H$_4$—O— | —CH$_2$—CH=CH—CH$_2$— | | |
| 205 | 3-F—C$_6$H$_4$—O— | —CH$_2$—CH=CH—CH$_2$— | | |
| 206 | 4-F—C$_6$H$_4$—O— | —CH$_2$—CH=CH—CH$_2$— | | |
| 207 | 2-Cl—C$_6$H$_4$—O— | —CH$_2$—CH=CH—CH$_2$— | | |
| 208 | 3-Cl—C$_6$H$_4$—O— | —CH$_2$—CH=CH—CH$_2$— | | |
| 209 | 4-Cl—C$_6$H$_4$—O— | —CH$_2$—CH=CH—CH$_2$— | | |
| 210 | C$_6$H$_5$—O— | —(CH$_2$)$_5$— | | |
| 211 | 2-Cl—C$_6$H$_4$—O— | —(CH$_2$)$_5$— | | |
| 212 | 3-Cl—C$_6$H$_4$—O— | —(CH$_2$)$_5$— | | |
| 213 | 4-Cl—C$_6$H$_4$—O— | —(CH$_2$)$_5$— | | |
| 214 | 2-F—C$_6$H$_4$—O— | —(CH$_2$)$_5$— | | |
| 215 | 3-F—C$_6$H$_4$—O— | —(CH$_2$)$_5$— | | |
| 216 | 4-F—C$_6$H$_4$—O— | —(CH$_2$)$_5$— | | |
| 217 | 2-CH$_3$—C$_6$H$_4$—O— | —(CH$_2$)$_5$— | | |
| 218 | 3-CH$_3$—C$_6$H$_4$—O— | —(CH$_2$)$_5$— | | |
| 219 | 4-CH$_3$—C$_6$H$_4$—O— | —(CH$_2$)$_5$— | | |
| 220 | 2-CH$_3$O—C$_6$H$_4$—O | —(CH$_2$)$_5$— | | |
| 221 | 3-CH$_3$O—C$_6$H$_4$—O | —(CH$_2$)$_5$— | | |
| 222 | 4-CH$_3$O—C$_6$H$_4$—O | —(CH$_2$)$_5$— | | |
| 223 | 4-t-C$_4$H$_9$—C$_6$H$_4$—O— | —(CH$_2$)$_5$— | | |
| 224 | 4-C$_2$H$_5$O—C$_6$H$_4$—O— | —(CH$_2$)$_5$— | | |
| 225 | 4-CF$_3$—C$_6$H$_4$—O— | —(CH$_2$)$_5$— | | |
| 226 | 4-C$_6$H$_5$—C$_6$H$_4$—O— | —(CH$_2$)$_5$— | | |
| 227 | 4-(C$_6$H$_5$—CH$_2$—O)—C$_6$H$_4$—O— | —(CH$_2$)$_5$— | | |
| 228 | 2,4,6-Cl$_3$—C$_6$H$_2$—O— | —(CH$_2$)$_5$— | | |
| 229 | 2,4,6-(CH$_3$)$_3$—C$_6$H$_2$—O— | —(CH$_2$)$_5$— | | |
| 230 | 1-naphthyl-O— | —(CH$_2$)$_5$— | | |
| 231 | 2-naphthyl-O— | —(CH$_2$)$_5$— | | |
| 232 | C$_6$H$_5$—CH$_2$—O— | —(CH$_2$)$_5$— | | |
| 233 | C$_6$H$_5$—O— | —(CH$_2$)$_6$— | | |
| 234 | 2-Cl—C$_6$H$_4$—O— | —(CH$_2$)$_6$— | | |
| 235 | 3-Cl—C$_6$H$_4$—O— | —(CH$_2$)$_6$— | | |
| 236 | 4-Cl—C$_6$H$_4$—O— | —(CH$_2$)$_6$— | | |
| 237 | 2-F—C$_6$H$_4$—O— | —(CH$_2$)$_6$— | | |
| 238 | 3-F—C$_6$H$_4$—O— | —(CH$_2$)$_6$— | | |
| 239 | 4-F—C$_6$H$_4$—O— | —(CH$_2$)$_6$— | | |
| 240 | 2-CH$_3$—C$_6$H$_4$—O— | —(CH$_2$)$_6$— | | |
| 241 | 3-CH$_3$—C$_6$H$_4$—O— | —(CH$_2$)$_6$— | | |
| 242 | 4-CH$_3$—C$_6$H$_4$—O— | —(CH$_2$)$_6$— | | |
| 243 | 2-CH$_3$O—C$_6$H$_4$—O— | —(CH$_2$)$_6$— | | |
| 244 | 3-CH$_3$O—C$_6$H$_4$—O— | —(CH$_2$)$_6$— | | |
| 245 | 4-CH$_3$O—C$_6$H$_4$—O— | —(CH$_2$)$_6$— | | |
| 246 | 4-t-C$_4$H$_9$—C$_6$H$_4$—O— | —(CH$_2$)$_6$— | | |
| 247 | 4-C$_2$H$_5$O—C$_6$H$_4$—O | —(CH$_2$)$_6$— | | |
| 248 | 4-CF$_3$—C$_6$H$_4$—O— | —(CH$_2$)$_6$— | | |
| 249 | 4-C$_6$H$_5$—C$_6$H$_4$—O— | —(CH$_2$)$_6$— | | |
| 250 | 4-(C$_6$H$_5$—CH$_2$—O)—C$_6$H$_4$—O— | —(CH$_2$)$_6$— | | |
| 251 | 2,4,6-Cl$_3$—C$_6$H$_2$—O— | —(CH$_2$)$_6$— | | |
| 252 | 2,4,6-(CH$_3$)$_3$—C$_6$H$_2$—O— | —(CH$_2$)$_6$— | | |
| 253 | 1-naphthyl-O— | —(CH$_2$)$_6$— | | |
| 254 | 2-naphthyl-O— | —(CH$_2$)$_6$— | | |
| 255 | C$_6$H$_5$—CH$_2$—O— | —(CH$_2$)$_6$— | | |
| 256 | C$_6$H$_5$—O— | —(CH$_2$)$_7$— | | |
| 257 | 2-Cl—C$_6$H$_4$—O— | —(CH$_2$)$_7$— | | |
| 258 | 3-Cl—C$_6$H$_4$—O— | —(CH$_2$)$_7$— | | |
| 259 | 4-Cl—C$_6$H$_4$—O— | —(CH$_2$)$_7$— | | |
| 260 | 2-F—C$_6$H$_4$—O— | —(CH$_2$)$_7$— | | |
| 261 | 3-F—C$_6$H$_4$—O— | —(CH$_2$)$_7$— | | |
| 262 | 4-F—C$_6$H$_4$—O— | —(CH$_2$)$_7$— | | |
| 263 | 2-CH$_3$—C$_6$H$_4$—O— | —(CH$_2$)$_7$— | | |
| 264 | 3-CH$_3$—C$_6$H$_4$—O— | —(CH$_2$)$_7$— | | |
| 265 | 4-CH$_3$—C$_6$H$_4$—O— | —(CH$_2$)$_7$— | | |
| 266 | 2-CH$_3$O—C$_6$H$_4$—O— | —(CH$_2$)$_7$— | | |
| 267 | 3-CH$_3$O—C$_6$H$_4$—O— | —(CH$_2$)$_7$— | | |

TABLE 1-continued

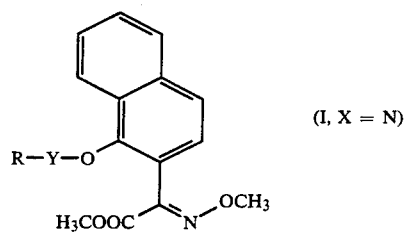

(I, X = N)

| Comp. no. | R | Y | mp (°C.) | IR (cm$^{-1}$) |
|---|---|---|---|---|
| 268 | 4-CH$_3$O—C$_6$H$_4$—O— | —(CH$_2$)$_7$— | | |
| 269 | 4-t-C$_4$H$_9$—C$_6$H$_4$—O— | —(CH$_2$)$_7$— | | |
| 270 | 4-C$_2$H$_5$O—C$_6$H$_4$—O— | —(CH$_2$)$_7$— | | |
| 271 | 4-CF$_3$—C$_6$H$_4$—O— | —(CH$_2$)$_7$— | | |
| 272 | 4-C$_6$H$_5$—C$_6$H$_4$—O— | —(CH$_2$)$_7$— | | |
| 273 | 2,4,6-(Cl$_3$)$_3$—C$_6$H$_2$—O— | —(CH$_2$)$_7$— | | |
| 274 | 2,4,6-(CH$_3$)$_3$—C$_6$H$_2$—O— | —(CH$_2$)$_7$— | | |
| 275 | 1-naphthyl-O— | —(CH$_2$)$_7$— | | |
| 276 | 2-naphthyl-O— | —(CH$_2$)$_7$— | | |
| 277 | 4-(C$_6$H$_5$—CH$_2$—O)C$_6$H$_4$—O— | —(CH$_2$)$_7$— | | |
| 278 | C$_6$H$_5$—CH$_2$—O— | —(CH$_2$)$_7$— | | |
| 279 | C$_6$H$_5$—O— | —(CH$_2$)$_8$— | | |
| 280 | 2-Cl—C$_6$H$_4$—O— | —(CH$_2$)$_8$— | | |
| 281 | 3-Cl—C$_6$H$_4$—O— | —(CH$_2$)$_8$— | | |
| 282 | 4-Cl—C$_6$H$_4$—O— | —(CH$_2$)$_8$— | | |
| 283 | 2-F—C$_6$H$_4$—O— | —(CH$_2$)$_8$— | | |
| 284 | 3-F—C$_6$H$_4$—O— | —(CH$_2$)$_8$— | | |
| 285 | 4-F—C$_6$H$_4$—O— | —(CH$_2$)$_8$— | | |
| 286 | 2-CH$_3$—C$_6$H$_4$—O— | —(CH$_2$)$_8$— | | |
| 287 | 3-CH$_3$—C$_6$H$_4$—O— | —(CH$_2$)$_8$— | | |
| 288 | 4-CH$_3$—C$_6$H$_4$—O— | —(CH$_2$)$_8$— | | |
| 289 | 2-CH$_3$O—C$_6$H$_4$—O— | —(CH$_2$)$_8$— | | |
| 290 | 3-CH$_3$O—C$_6$H$_4$—O— | —(CH$_2$)$_8$— | | |
| 291 | 4-CH$_3$O—C$_6$H$_4$—O— | —(CH$_2$)$_8$— | | |
| 292 | 4-t-C$_4$H$_9$—C$_6$H$_4$—O— | —(CH$_2$)$_8$— | | |
| 293 | 4-C$_2$H$_5$O—C$_6$H$_4$—O— | —(CH$_2$)$_8$— | | |
| 294 | 4-CF$_3$—C$_6$H$_4$—O— | —(CH$_2$)$_8$— | | |
| 295 | 4-C$_6$H$_5$—C$_6$H$_4$—O— | —(CH$_2$)$_8$— | | |
| 296 | 4-(C$_6$H$_5$—CH$_2$—O)—C$_6$H$_4$—O— | —(CH$_2$)$_8$— | | |
| 297 | 2,4,6-Cl$_3$—C$_6$H$_2$—O— | —(CH$_2$)$_8$— | | |
| 298 | 2,4,6-(CH$_3$)$_3$—C$_6$H$_2$—O— | —(CH$_2$)$_8$— | | |
| 299 | 1-naphthyl-O— | —(CH$_2$)$_8$— | | |
| 300 | 2-naphthyl-O— | —(CH$_2$)$_8$— | | |
| 301 | C$_6$H$_5$—CH$_2$—O— | —(CH$_2$)$_8$— | | |
| 302 | C$_6$H$_5$—O— | —(CH$_2$)$_9$— | | |
| 303 | C$_6$H$_5$—O— | —(CH$_2$)$_{10}$— | | |
| 304 | 2-Cl—C$_6$H$_4$—O— | —(CH$_2$)$_{10}$— | | |
| 305 | 3-Cl—C$_6$H$_4$—O— | —(CH$_2$)$_{10}$— | | |
| 306 | 4-Cl—C$_6$H$_4$—O— | —(CH$_2$)$_{10}$— | | |
| 307 | 2-F—C$_6$H$_4$—O— | —(CH$_2$)$_{10}$— | | |
| 308 | 3-F—C$_6$H$_4$—O— | —(CH$_2$)$_{10}$— | | |
| 309 | 4-F—C$_6$H$_4$—O— | —(CH$_2$)$_{10}$— | | |
| 310 | 2-CH$_3$—C$_6$H$_4$—O— | —(CH$_2$)$_{10}$— | | |
| 311 | 3-CH$_3$—C$_6$H$_4$—O— | —(CH$_2$)$_{10}$— | | |
| 312 | 4-CH$_3$—C$_6$H$_4$—O— | —(CH$_2$)$_{10}$— | | |
| 313 | 2-CH$_3$O—C$_6$H$_4$—O— | —(CH$_2$)$_{10}$— | | |
| 314 | 3-CH$_3$O—C$_6$H$_4$—O— | —(CH$_2$)$_{10}$— | | |
| 315 | 4-CH$_3$O—C$_6$H$_4$—O— | —(CH$_2$)$_{10}$— | | |
| 316 | 4-t-C$_4$H$_9$—C$_6$H$_4$—O— | —(CH$_2$)$_{10}$— | | |
| 317 | 4-C$_2$H$_5$O—C$_6$H$_4$—O— | —(CH$_2$)$_{10}$— | | |
| 318 | 4-CF$_3$—C$_6$H$_4$—O— | —(CH$_2$)$_{10}$— | | |
| 319 | 4-C$_6$H$_5$—C$_6$H$_4$—O— | —(CH$_2$)$_{10}$— | | |
| 320 | 4-(C$_6$H$_5$—CH$_2$—O)—C$_6$H$_4$—O— | —(CH$_2$)$_{10}$— | | |
| 321 | 2,4,6-Cl$_3$—C$_6$H$_2$—O— | —(CH$_2$)$_{10}$— | | |
| 322 | 2,4,6-(CH$_3$)$_3$—C$_6$H$_2$—O— | —(CH$_2$)$_{10}$— | | |
| 323 | 1-naphthyl-O— | —(CH$_2$)$_{10}$— | | |
| 324 | 2-naphthyl-O— | —(CH$_2$)$_{10}$— | | |
| 325 | C$_6$H$_5$—CH$_2$—O— | —(CH$_2$)$_{10}$— | | |
| 326 | 3,4-Cl$_2$—C$_6$H$_3$ | —CH$_2$— | resin | 2945, 1742, 1473, 1353, 1228, 1061, 1035, 819 |
| 327 | 3-C$_6$H$_5$O—C$_6$H$_4$ | —CH$_2$— | | |
| 328 | 4-C$_{12}$—H$_{25}$—C$_6$H$_4$ | —CH$_2$— | | |
| 329 | 2-Cl, 6-CN—C$_6$H$_3$ | —CH$_2$— | | |
| 330 | 3,4-(CH$_3$)$_2$—C$_6$H$_3$ | —CH$_2$— | | |
| 331 | 2-CH$_3$, 4-t-C$_4$H$_9$—C$_6$H$_3$ | —CH$_2$— | | |
| 332 | 2-Cl, 4-CH$_3$O—C$_6$H$_3$ | —CH$_2$— | | |
| 333 | 2,3,6-Cl$_3$—C$_6$H$_2$ | —CH$_2$— | | |

TABLE 2

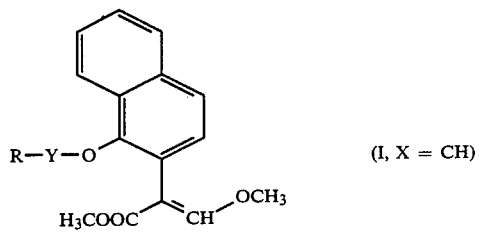

(I, X = CH)

| Comp. no. | R | Y | mp(°C.) | IR(cm$^{-1}$) |
|---|---|---|---|---|
| 1a | C$_6$H$_5$ | —CH$_2$— | | |
| 2a | 2-F—C$_6$H$_4$ | —CH$_2$— | | |
| 3a | 3-F—C$_6$H$_4$ | —CH$_2$— | | |
| 4a | 4-F—C$_6$H$_4$ | —CH$_2$— | | |
| 5a | 2,4-F$_2$—C$_6$H$_3$ | —CH$_2$— | | |
| 6a | 2-Cl—C$_6$H$_4$ | —CH$_2$— | | |
| 7a | 3-Cl—C$_6$H$_4$ | —CH$_2$— | | |
| 8a | 4-Cl—C$_6$H$_4$ | —CH$_2$— | | |
| 9a | 2,4-Cl$_2$—C$_6$H$_3$ | —CH$_2$— | | |
| 10a | 2,6-Cl$_2$—C$_6$H$_3$ | —CH$_2$— | | |
| 11a | 3,5-Cl$_2$—C$_6$H$_3$ | —CH$_2$— | | |
| 12a | 2,4,6-Cl$_3$—C$_6$H$_2$ | —CH$_2$— | | |
| 13a | 2-Br—C$_6$H$_4$ | —CH$_2$— | | |
| 14a | 3-Br—C$_6$H$_4$ | —CH$_2$— | | |
| 15a | 4-Br—C$_6$H$_4$ | —CH$_2$— | | |
| 16a | 2,4-Br$_2$—C$_6$H$_3$ | —CH$_2$— | | |
| 17a | 2-J—C$_6$H$_4$ | —CH$_2$— | | |
| 18a | 2-CH$_3$—C$_6$H$_4$ | —CH$_2$— | | |
| 19a | 3-CH$_3$—C$_6$H$_4$ | —CH$_2$— | | |
| 20a | 4-CH$_3$—C$_6$H$_4$ | —CH$_2$— | | |
| 21a | 2,4-(CH$_3$)$_2$—C$_6$H$_3$ | —CH$_2$— | | |
| 22a | 2,5-(CH$_3$)$_2$—C$_6$H$_3$ | —CH$_2$— | | |
| 23a | 2,4,6-(CH$_3$)$_3$—C$_6$H$_2$ | —CH$_2$— | | |
| 24a | 4-t-C$_4$H$_9$—C$_6$H$_4$ | —CH$_2$— | | |
| 25a | 4-i-C$_3$H$_7$—C$_6$H$_4$ | —CH$_2$— | | |
| 26a | 4-C$_2$H$_5$—C$_6$H$_4$ | —CH$_2$— | | |
| 27a | 2-CH$_3$O—C$_6$H$_4$ | —CH$_2$— | | |
| 28a | 3-CH$_3$O—C$_6$H$_4$ | —CH$_2$— | | |
| 29a | 4-CH$_3$O—C$_6$H$_4$ | —CH$_2$— | | |
| 30a | 4-C$_2$H$_5$O—C$_6$H$_4$ | —CH$_2$— | | |
| 31a | 4-i-C$_3$H$_7$O—C$_6$H$_4$ | —CH$_2$— | | |
| 32a | 2-CF$_3$—C$_6$H$_4$ | —CH$_2$— | | |
| 33a | 3-CF$_3$—C$_6$H$_4$ | —CH$_2$— | | |
| 34a | 4-CF$_3$—C$_6$H$_4$ | —CH$_2$— | | |
| 35a | 2-CN—C$_6$H$_4$ | —CH$_2$— | | |
| 36a | 3-CN—C$_6$H$_4$ | —CH$_2$— | | |
| 37a | 4-CN—C$_6$H$_4$ | —CH$_2$— | | |
| 38a | 2-NO$_2$—C$_6$H$_4$ | —CH$_2$— | | |
| 39a | 3-NO$_2$—C$_6$H$_4$ | —CH$_2$— | | |
| 40a | 4-NO$_2$—C$_6$H$_4$ | —CH$_2$— | | |
| 41a | 3-C$_6$H$_5$—C$_6$H$_4$ | —CH$_2$— | | |
| 42a | 4-C$_6$H$_5$—C$_6$H$_4$ | —CH$_2$— | | |
| 43a | 4-C$_6$H$_5$O—C$_6$H$_4$ | —CH$_2$— | | |
| 44a | 2-F,3-CH$_3$—C$_6$H$_3$ | —CH$_2$— | | |
| 45a | 2-Cl,3-CH$_3$—C$_6$H$_3$ | —CH$_2$— | | |
| 46a | 2-Br,3-CH$_3$—C$_6$H$_3$ | —CH$_2$— | | |
| 47a | 2-Cl,3-i-C$_3$H$_7$—C$_6$H$_3$ | —CH$_2$— | | |
| 48a | 2-CH$_3$,3-i-C$_3$H$_7$—C$_6$H$_3$ | —CH$_2$— | | |
| 49a | 2-CH$_3$,3-C$_6$H$_5$—C$_6$H$_3$ | —CH$_2$— | | |
| 50a | 2-Cl,3-C$_6$H$_5$—C$_6$H$_3$ | —CH$_2$— | | |
| 51a | 2-CH$_3$O,3-i-C$_3$H$_7$—C$_6$H$_3$ | —CH$_2$— | | |
| 52a | 2,4,5-Cl$_3$—C$_6$H$_2$ | —CH$_2$— | | |
| 53a | 2,4,5-(CH$_3$)$_3$—C$_6$H$_2$ | —CH$_2$— | | |
| 54a | 2-CH$_3$O,5-NO$_2$—C$_6$H$_3$ | —CH$_2$— | | |
| 55a | 2,5-Cl$_2$—C$_6$H$_3$ | —CH$_2$— | | |
| 56a | 2,5-F$_2$—C$_6$H$_3$ | —CH$_2$— | | |
| 57a | 2-Cl,5-CH$_3$—C$_6$H$_3$ | —CH$_2$— | | |
| 58a | 2-F,3-CH$_3$—C$_6$H$_3$ | —CH$_2$— | | |
| 59a | 2,3-F$_2$—C$_6$H$_3$ | —CH$_2$— | | |
| 60a | 2,3-Cl$_2$—C$_6$H$_3$ | —CH$_2$— | | |
| 61a | 2-F,3-Cl—C$_6$H$_3$ | —CH$_2$— | | |
| 62a | 2-F,4-Br—C$_6$H$_3$ | —CH$_2$— | | |
| 63a | 2,6-F$_2$—C$_6$H$_3$ | —CH$_2$— | | |
| 64a | 2-F,6-Cl—C$_6$H$_3$ | —CH$_2$— | | |
| 65a | 2-Cl,6-CF$_3$—C$_6$H$_3$ | —CH$_2$— | | |
| 66a | 2,3,4,5,6-(CH$_3$)$_5$—C$_6$ | —CH$_2$— | | |
| 67a | 2,3,4,5,6-F$_5$—C$_6$ | —CH$_2$— | | |
| 68a | 2-CH$_3$,4-Cl—C$_6$H$_3$ | —CH$_2$— | | |
| 69a | 2-Cl,4-CH$_3$—C$_6$H$_3$ | —CH$_2$— | | |

TABLE 2-continued $$\text{R—Y—O-naphthyl-C(=CH-OCH}_3\text{)-COOCH}_3 \quad (I, X = CH)$$

| Comp. no. | R | Y | mp(°C.) | IR(cm$^{-1}$) |
|---|---|---|---|---|
| 70a | 2-CH$_3$O,4-CH$_3$—C$_6$H$_3$ | —CH$_2$— | | |
| 71a | 4-CH$_3$O,2-CH$_3$—C$_6$H$_3$ | —CH$_2$— | | |
| 72a | C$_6$H$_5$—O— | —CH$_2$—CH$_2$— | | |
| 73a | 2-F—C$_6$H$_4$—O— | —CH$_2$—CH$_2$— | | |
| 74a | 3-F—C$_6$H$_4$—O— | —CH$_2$—CH$_2$— | | |
| 75a | 4-F—C$_6$H$_4$—O— | —CH$_2$—CH$_2$— | | |
| 76a | 2-Cl—C$_6$H$_4$—O— | —CH$_2$—CH$_2$— | | |
| 77a | 3-Cl—C$_6$H$_4$—O— | —CH$_2$—CH$_2$— | | |
| 78a | 4-Cl—C$_6$H$_4$—O— | —CH$_2$—CH$_2$— | | |
| 79a | 2-CH$_3$—C$_6$H$_4$—O— | —CH$_2$—CH$_2$— | | |
| 80a | 3-CH$_3$—C$_6$H$_4$—O— | —CH$_2$—CH$_2$— | | |
| 81a | 4-CH$_3$—C$_6$H$_4$—O— | —CH$_2$—CH$_2$— | | |
| 82a | 2-CH$_3$O—C$_6$H$_4$—O— | —CH$_2$—CH$_2$— | | |
| 83a | 3-CH$_3$O—C$_6$H$_4$—O— | —CH$_2$—CH$_2$— | | |
| 84a | 4-CH$_3$O—C$_6$H$_4$—O— | —CH$_2$—CH$_2$— | | |
| 85a | 4-t-C$_4$H$_9$—C$_6$H$_4$—O— | —CH$_2$—CH$_2$— | | |
| 86a | 4-C$_2$H$_5$O—C$_6$H$_4$—O— | —CH$_2$—CH$_2$— | | |
| 87a | 4-CF$_3$—C$_6$H$_4$—O— | —CH$_2$—CH$_2$— | | |
| 88a | 4-C$_6$H$_5$—C$_6$H$_4$—O— | —CH$_2$—CH$_2$— | | |
| 89a | 4-(C$_6$H$_5$—CH$_2$—O)—C$_6$H$_4$—O— | —CH$_2$—CH$_2$— | | |
| 90a | 2,4,6-Cl$_3$—C$_6$H$_2$—O— | —CH$_2$—CH$_2$— | | |
| 91a | 2,4,6-(CH$_3$)$_3$—C$_6$H$_2$—O— | —CH$_2$—CH$_2$— | | |
| 92a | 1-naphthyl-O— | —CH$_2$—CH$_2$— | | |
| 93a | 2-naphthyl-O— | —CH$_2$—CH$_2$— | | |
| 94a | 2-Br—C$_6$H$_4$—O— | —CH$_2$—CH$_2$— | | |
| 95a | 3-Br—C$_6$H$_4$—O— | —CH$_2$—CH$_2$— | | |
| 96a | 4-Br—C$_6$H$_4$—O— | —CH$_2$—CH$_2$— | | |
| 97a | 2-CF$_3$—C$_6$H$_4$—O— | —CH$_2$—CH$_2$— | | |
| 98a | 3-CF$_3$—C$_6$H$_4$—O— | —CH$_2$—CH$_2$— | | |
| 99a | 4-CN—C$_6$H$_4$—O— | —CH$_2$—CH$_2$— | | |
| 100a | 4-CH$_3$CO—C$_6$H$_4$—O— | —CH$_2$—CH$_2$— | | |
| 101a | 3-(CH$_3$)$_2$N—C$_6$H$_4$—O— | —CH$_2$—CH$_2$— | | |
| 102a | 4-CH$_3$S—C$_6$H$_4$—O— | —CH$_2$—CH$_2$— | | |
| 103a | 2-C$_2$H$_5$O—C$_6$H$_4$—O— | —CH$_2$—CH$_2$— | | |
| 104a | 4-t-C$_4$H$_9$—C$_6$H$_4$—O— | —CH$_2$—CH$_2$— | | |
| 105a | 2,4-Cl$_2$—H$_6$H$_3$—O— | —CH$_2$—CH$_2$— | | |
| 106a | 3,4-Cl$_2$—C$_6$H$_3$—O— | —CH$_2$—CH$_2$— | | |
| 107a | 2,5-Cl$_2$—C$_6$H$_3$—O— | —CH$_2$—CH$_2$— | | |
| 108a | 2,6-Cl$_2$—C$_6$H$_3$—O— | —CH$_2$—CH$_2$— | | |
| 109a | 2,4,5-Cl$_3$—C$_6$H$_2$—O— | —CH$_2$—CH$_2$— | | |
| 110a | 2-Cl,4-F—C$_6$H$_3$—O— | —CH$_2$—CH$_2$— | | |
| 111a | 2-Cl,4-Br—C$_6$H$_3$—O— | —CH$_2$—CH$_2$— | | |
| 112a | 2,4-(CH$_3$)$_2$—C$_6$H$_3$—O— | —CH$_2$—CH$_2$— | | |
| 113a | 2-CH$_3$,4-t-C$_4$H$_9$—C$_6$H$_3$—O | —CH$_2$—CH$_2$— | | |
| 114a | 2-CH$_3$,4-Cl—C$_6$H$_3$—O— | —CH$_2$—CH$_2$— | | |
| 115a | 2-CH$_3$,4,6-Cl$_2$—C$_6$H$_2$—O— | —CH$_2$—CH$_2$— | | |
| 116a | 2,6-(CH$_3$)$_2$—C$_6$H$_3$—O— | —CH$_2$—CH$_2$— | | |
| 117a | 2,5,6-(CH$_3$)$_3$—C$_6$H$_2$—O— | —CH$_2$—CH$_2$— | | |
| 118a | 2,4,5-(CH$_3$)$_3$—C$_6$H$_2$—O— | —CH$_2$—CH$_2$— | | |
| 119a | 2-i-C$_3$H$_7$,5-CH$_3$—C$_6$H$_3$—O— | —CH$_2$—CH$_2$— | | |
| 120a | 3,5-(C$_2$H$_5$)$_2$—C$_6$H$_3$—O— | —CH$_2$—CH$_2$— | | |
| 121a | 2,4,6-(sec-C$_4$H$_9$)$_3$—C$_6$H$_2$—O— | —CH$_2$—CH$_2$— | | |
| 122a | 3,5-(CH$_3$O)$_2$—C$_6$H$_3$—O— | —CH$_2$—CH$_2$— | | |
| 123a | 2-CH$_3$O,4-CH$_3$—C$_6$H$_3$—O— | —CH$_2$—CH$_2$— | | |
| 124a | 2,6-(CH$_3$)$_2$,4-CH$_3$S—C$_6$H$_2$—O— | —CH$_2$—CH$_2$— | | |
| 125a | 2-Cl,5-CH$_3$O—C$_6$H$_3$—O— | —CH$_2$—CH$_2$— | | |
| 126a | 2-CH$_3$,4-CH$_3$S—C$_6$H$_3$—O— | —CH$_2$—CH$_2$— | | |
| 127a | 2,6-(CH$_3$O)$_2$—C$_6$H$_3$—O— | —CH$_2$—CH$_2$— | | |
| 128a | 2-Cl,4-C$_6$H$_5$—C$_6$H$_3$—O— | —CH$_2$—CH$_2$— | | |
| 129a | 2-Cl,4-CH$_3$—C$_6$H$_3$—O— | —CH$_2$—CH$_2$— | | |
| 130a | 2-CH$_3$,6-i-C$_3$H$_7$—C$_6$H$_3$—O— | —CH$_2$—CH$_2$— | | |
| 131a | 3-t-C$_4$H$_9$,4-CH$_3$O—C$_6$H$_3$—O— | —CH$_2$—CH$_2$— | | |
| 132a | 2,4-(CH$_3$)$_2$-1-naphthyl-O— | —CH$_2$—CH$_2$— | | |
| 133a | C$_6$H$_5$—S | —CH$_2$—CH$_2$— | | |
| 134a | 4-Cl—C$_6$H$_4$—S | —CH$_2$—CH$_2$— | | |
| 135a | 2,4,6-Cl$_3$—C$_6$H$_2$—O— | —CH$_2$—CH(CH$_3$)— | | |
| 136a | C$_6$H$_5$—O— | —CH$_2$—CH(CH$_3$)— | | |
| 137a | C$_6$H$_5$—O— | —(CH$_2$)$_3$— | | |
| 138a | 2-F—C$_6$H$_4$—O— | —(CH$_2$)$_3$— | | |

TABLE 2-continued

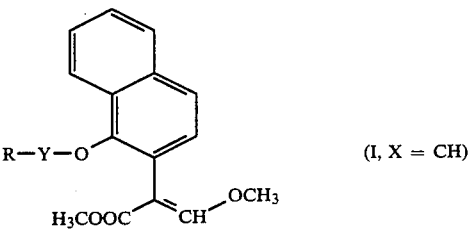

(I, X = CH)

| Comp. no. | R | Y | mp(°C.) | IR(cm$^{-1}$) |
|---|---|---|---|---|
| 139a | 3-F—C$_6$H$_4$—O— | —(CH$_2$)$_3$— | | |
| 140a | 4-F—C$_6$H$_4$—O— | —(CH$_2$)$_3$— | | |
| 141a | 2-Cl—C$_6$H$_4$—O— | —(CH$_2$)$_3$— | | |
| 142a | 3-Cl—C$_6$H$_4$—O— | —(CH$_2$)$_3$— | | |
| 143a | 4-Cl—C$_6$H$_4$—O— | —(CH$_2$)$_3$— | | |
| 144a | 2-CH$_3$—C$_6$H$_4$—O— | —(CH$_2$)$_3$— | | |
| 145a | 3-CH$_3$—C$_6$H$_4$—O— | —(CH$_2$)$_3$— | | |
| 146a | 4-CH$_3$—C$_6$H$_4$—O— | —(CH$_2$)$_3$— | | |
| 147a | 2-CH$_3$O—C$_6$H$_4$—O— | —(CH$_2$)$_3$— | | |
| 148a | 3-CH$_3$O—C$_6$H$_4$—O— | —(CH$_2$)$_3$— | | |
| 149a | 4-CH$_3$O—C$_6$H$_4$—O— | —(CH$_2$)$_3$— | | |
| 150a | 4-t-C$_4$H$_9$—C$_6$H$_4$—O— | —(CH$_2$)$_3$— | | |
| 151a | 4-C$_2$H$_5$O—C$_6$H$_4$—O— | —(CH$_2$)$_3$— | | |
| 152a | 4-CF$_3$—C$_6$H$_4$—O— | —(CH$_2$)$_3$— | | |
| 153a | 4-C$_6$H$_5$—C$_6$H$_4$—O— | —(CH$_2$)$_3$— | | |
| 154a | 4-(C$_6$H$_5$—CH$_2$—O)—C$_6$H$_4$—O— | —(CH$_2$)$_3$— | | |
| 155a | 2,4,6-Cl$_3$—C$_6$H$_2$—O— | —(CH$_2$)$_3$— | | |
| 156a | 2,4,6-(CH$_3$)$_3$—C$_6$H$_2$—O— | —(CH$_2$)$_3$— | | |
| 157a | 1-naphthyl-O— | —(CH$_2$)$_3$— | | |
| 158a | 2-naphthyl-O— | —(CH$_2$)$_3$— | | |
| 159a | 2,4-Cl$_2$—C$_6$H$_3$—O— | —(CH$_2$)$_3$— | | |
| 160a | 3,5-Cl$_2$—C$_6$H$_3$—O— | —(CH$_2$)$_3$— | | |
| 161a | 3,4-Cl$_2$—C$_6$H$_3$—O— | —(CH$_2$)$_3$— | | |
| 162a | 2,6-(CH$_3$)$_2$—C$_6$H$_3$—O— | —(CH$_2$)$_3$— | | |
| 163a | 2,4-(CH$_3$)$_2$—C$_6$H$_3$—O— | —(CH$_2$)$_3$— | | |
| 164a | 3-CF$_3$—C$_6$H$_4$—O— | —(CH$_2$)$_3$— | | |
| 165a | 2-Cl,4-CH$_3$—C$_6$H$_3$—O— | —(CH$_2$)$_3$— | | |
| 166a | C$_6$H$_5$—S— | —(CH$_2$)$_3$— | | |
| 167a | C$_6$H$_5$—CH$_2$—O— | —(CH$_2$)$_3$— | | |
| 168a | C$_6$H$_5$—O— | —(CH$_2$)$_4$— | | |
| 169a | 2-F—C$_6$H$_4$—O— | —(CH$_2$)$_4$— | | |
| 170a | 3-F—C$_6$H$_4$—O— | —(CH$_2$)$_4$— | | |
| 171a | 4-F—C$_6$H$_4$—O— | —(CH$_2$)$_4$— | | |
| 172a | 2-CH$_3$—C$_6$H$_4$—O— | —(CH$_2$)$_4$— | | |
| 173a | 3-CH$_3$—C$_6$H$_4$—O— | —(CH$_2$)$_4$— | | |
| 174a | 4-CH$_3$—C$_6$H$_4$—O— | —(CH$_2$)$_4$— | | |
| 175a | 2-CH$_3$O—C$_6$H$_4$—O— | —(CH$_2$)$_4$— | | |
| 176a | 3-CH$_3$O—C$_6$H$_4$—O— | —(CH$_2$)$_4$— | | |
| 177a | 4-CH$_3$O—C$_6$H$_4$—O— | —(CH$_2$)$_4$— | | |
| 178a | 4-t-C$_4$H$_9$—C$_6$H$_4$—O— | —(CH$_2$)$_4$— | | |
| 179a | 4-C$_2$H$_5$O—C$_6$H$_4$—O— | —(CH$_2$)$_4$— | | |
| 180a | 4-CF$_3$—C$_6$H$_4$—O— | —(CH$_2$)$_4$— | | |
| 181a | 4-C$_6$H$_5$—C$_6$H$_4$—O— | —(CH$_2$)$_4$— | | |
| 182a | 4-(C$_6$H$_5$—CH$_2$—O)—C$_6$H$_4$— | —(CH$_2$)$_4$— | | |
| 183a | 2,4,6-Cl$_3$—C$_6$H$_2$—O— | —(CH$_2$)$_4$— | | |
| 184a | 2,4,6-(CH$_3$)$_3$—C$_6$H$_2$—O— | —(CH$_2$)$_4$— | | |
| 185a | 1-naphthyl-O— | —(CH$_2$)$_4$— | | |
| 186a | 2-naphthyl-O— | —(CH$_2$)$_4$— | | |
| 187a | 3-CF$_3$—C$_6$H$_4$—O— | —(CH$_2$)$_4$— | | |
| 188a | 3-iso-C$_3$H$_7$—C$_6$H$_4$—O— | —(CH$_2$)$_4$— | | |
| 189a | 4-iso-C$_3$H$_7$—C$_6$H$_4$—O— | —(CH$_2$)$_4$— | | |
| 190a | 4-t-C$_4$H$_9$—C$_6$H$_4$—O— | —(CH$_2$)$_4$— | | |
| 191a | 4-t-C$_4$H$_9$—C$_6$H$_4$—O— | —(CH$_2$)$_4$— | | |
| 192a | 3-C$_6$H$_5$—C$_6$H$_4$—O— | —(CH$_2$)$_4$— | | |
| 193a | 2,4-Cl$_2$—C$_6$H$_3$—O— | —(CH$_2$)$_4$— | | |
| 194a | 3,4-Cl$_2$—C$_6$H$_3$—O— | —(CH$_2$)$_4$— | | |
| 195a | 3,5-Cl$_2$—C$_6$H$_3$—O— | —(CH$_2$)$_4$— | | |
| 196a | 2,6-Cl$_2$—C$_6$H$_3$—O— | —(CH$_2$)$_4$— | | |
| 197a | 2-Cl,4-CH$_3$—C$_6$H$_3$—O— | —(CH$_2$)$_4$— | | |
| 198a | 2,6-(CH$_3$)$_2$—C$_6$H$_3$—O— | —(CH$_2$)$_4$— | | |
| 199a | 2,5-(CH$_3$)$_2$—C$_6$H$_3$—O— | —(CH$_2$)$_4$— | | |
| 200a | 4-CN—C$_6$H$_4$—O— | —(CH$_2$)$_4$— | | |
| 201a | C$_6$H$_5$—S— | —(CH$_2$)$_4$— | | |
| 202a | C$_6$H$_5$—CH$_2$—O— | —(CH$_2$)$_4$— | | |
| 203a | C$_6$H$_5$—O— | —CH$_2$—CH=CH—CH$_2$— | | |
| 204a | 2-F—C$_6$H$_4$—O— | —CH$_2$—CH=CH—CH$_2$— | | |
| 205a | 3-F—C$_6$H$_4$—O— | —CH$_2$—CH=CH—CH$_2$— | | |
| 206a | 4-F—C$_6$H$_4$—O— | —CH$_2$—CH=CH—CH$_2$— | | |
| 207a | 2-Cl—C$_6$H$_4$—O— | —CH$_2$—CH=CH—CH$_2$— | | |

TABLE 2-continued

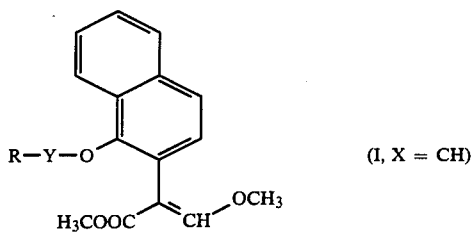

(I, X = CH)

| Comp. no. | R | Y | mp(°C.) | IR(cm$^{-1}$) |
|---|---|---|---|---|
| 208a | 3-Cl—C$_6$H$_4$—O— | —CH$_2$—CH=CH—CH$_2$— | | |
| 209a | 4-Cl—C$_6$H$_4$—O— | —CH$_2$—CH=CH—CH$_2$— | | |
| 210a | C$_6$H$_5$—O— | —(CH$_2$)$_5$— | | |
| 211a | 2-Cl—C$_6$H$_4$—O— | —(CH$_2$)$_5$— | | |
| 212a | 3-Cl—C$_6$H$_4$—O— | —(CH$_2$)$_5$— | | |
| 213a | 4-Cl—C$_6$H$_4$—O— | —(CH$_2$)$_5$— | | |
| 214a | 2-F—C$_6$H$_4$—O— | —(CH$_2$)$_5$— | | |
| 215a | 3-F—C$_6$H$_4$—O— | —(CH$_2$)$_5$— | | |
| 216a | 4-F—C$_6$H$_4$—O— | —(CH$_2$)$_5$— | | |
| 217a | 2-CH$_3$—C$_6$H$_4$—O— | —(CH$_2$)$_5$— | | |
| 218a | 3-CH$_3$—C$_6$H$_4$—O— | —(CH$_2$)$_5$— | | |
| 219a | 4-CH$_3$—C$_6$H$_4$—O— | —(CH$_2$)$_5$— | | |
| 220a | 2-CH$_3$O—C$_6$H$_4$—O— | —(CH$_2$)$_5$— | | |
| 221a | 3-CH$_3$O—C$_6$H$_4$—O— | —(CH$_2$)$_5$— | | |
| 222a | 4-CH$_3$O—C$_6$H$_4$—O— | —(CH$_2$)$_5$— | | |
| 223a | 4-t-C$_4$H$_9$—C$_6$H$_4$—O— | —(CH$_2$)$_5$— | | |
| 224a | 4-C$_2$H$_5$O—C$_6$H$_4$—O— | —(CH$_2$)$_5$— | | |
| 225a | 4-CF$_3$—C$_6$H$_4$—O— | —(CH$_2$)$_5$— | | |
| 226a | 4-C$_6$H$_5$—C$_6$H$_4$—O— | —(CH$_2$)$_5$— | | |
| 227a | 4-(C$_6$H$_5$—CH$_2$—O)—C$_6$H$_4$—O— | —(CH$_2$)$_5$— | | |
| 228a | 2,4,6-Cl$_3$—C$_6$H$_2$—O— | —(CH$_2$)$_5$— | | |
| 229a | 2,4,6-(CH$_3$)$_3$—C$_6$H$_2$—O— | —(CH$_2$)$_5$— | | |
| 230a | 1-naphthyl-O— | —(CH$_2$)$_5$— | | |
| 231a | 2-naphthyl-O— | —(CH$_2$)$_5$— | | |
| 232a | C$_6$H$_5$—CH$_2$—O— | —(CH$_2$)$_5$— | | |
| 233a | C$_6$H$_5$—O— | —(CH$_2$)$_6$— | | |
| 234a | 2-Cl—C$_6$H$_4$—O— | —(CH$_2$)$_6$— | | |
| 235a | 3-Cl—C$_6$H$_4$—O— | —(CH$_2$)$_6$— | | |
| 236a | 4-Cl—C$_6$H$_4$—O— | —(CH$_2$)$_6$— | | |
| 237a | 2-F—C$_6$H$_4$—O— | —(CH$_2$)$_6$— | | |
| 238a | 3-F—C$_6$H$_4$—O— | —(CH$_2$)$_6$— | | |
| 239a | 4-F—C$_6$H$_4$—O— | —(CH$_2$)$_6$— | | |
| 240a | 2-CH$_3$—C$_6$H$_4$—O— | —(CH$_2$)$_6$— | | |
| 241a | 3-CH$_3$—C$_6$H$_4$—O— | —(CH$_2$)$_6$— | | |
| 242a | 4-CH$_3$—C$_6$H$_4$—O— | —(CH$_2$)$_6$— | | |
| 243a | 2-CH$_3$O—C$_6$H$_4$—O— | —(CH$_2$)$_6$— | | |
| 244a | 3-CH$_3$O—C$_6$H$_4$—O— | —(CH$_2$)$_6$— | | |
| 245a | 4-CH$_3$O—C$_6$H$_4$—O— | —(CH$_2$)$_6$— | | |
| 246a | 4-t-C$_4$H$_9$—C$_6$H$_4$—O— | —(CH$_2$)$_6$— | | |
| 247a | 4-C$_2$H$_5$O—C$_6$H$_4$—O— | —(CH$_2$)$_6$— | | |
| 248a | 4-CF$_3$—C$_6$H$_4$—O— | —(CH$_2$)$_6$— | | |
| 249a | 4-C$_6$H$_5$—C$_6$H$_4$—O— | —(CH$_2$)$_6$— | | |
| 250a | 4-(C$_6$H$_5$—CH$_2$—O)—C$_6$H$_4$—O— | —(CH$_2$)$_6$— | | |
| 251a | 2,4,6-Cl$_3$—C$_6$H$_2$—O— | —(CH$_2$)$_6$— | | |
| 252a | 2,4,6-(CH$_3$)$_3$—C$_6$H$_2$—O— | —(CH$_2$)$_6$— | | |
| 253a | 1-naphthyl-O— | —(CH$_2$)$_6$— | | |
| 254a | 2-naphthyl-O— | —(CH$_2$)$_6$— | | |
| 255a | C$_6$H$_5$—CH$_2$—O— | —(CH$_2$)$_6$— | | |
| 256a | C$_6$H$_5$—O— | —(CH$_2$)$_7$— | | |
| 257a | 2-Cl—C$_6$H$_4$—O— | —(CH$_2$)$_7$— | | |
| 258a | 3-Cl—C$_6$H$_4$—O— | —(CH$_2$)$_7$— | | |
| 259a | 4-Cl—C$_6$H$_4$—O— | —(CH$_2$)$_7$— | | |
| 260a | 2-F—C$_6$H$_4$—O— | —(CH$_2$)$_7$— | | |
| 261a | 3-F—C$_6$H$_4$—O— | —(CH$_2$)$_7$— | | |
| 262a | 4-F—C$_6$H$_4$—O— | —(CH$_2$)$_7$— | | |
| 263a | 2-CH$_3$—C$_6$H$_4$—O— | —(CH$_2$)$_7$— | | |
| 264a | 3-CH$_3$—C$_6$H$_4$—O— | —(CH$_2$)$_7$— | | |
| 265a | 4-CH$_3$—C$_6$H$_4$—O— | —(CH$_2$)$_7$— | | |
| 266a | 2-CH$_3$O—C$_6$H$_4$—O— | —(CH$_2$)$_7$— | | |
| 267a | 3-CH$_3$O—C$_6$H$_4$—O— | —(CH$_2$)$_7$— | | |
| 268a | 4-CH$_3$O—C$_6$H$_4$—O— | —(CH$_2$)$_7$— | | |
| 269a | 4-t-C$_4$H$_9$—C$_6$H$_4$—O— | —(CH$_2$)$_7$— | | |
| 270a | 4-C$_2$H$_5$O—C$_6$H$_4$—O— | —(CH$_2$)$_7$— | | |
| 271a | 4-CF$_3$—C$_6$H$_4$—O— | —(CH$_2$)$_7$— | | |
| 272a | 4-C$_6$H$_5$—C$_6$H$_4$—O— | —(CH$_2$)$_7$— | | |
| 273a | 2,4,6-(Cl$_3$)$_3$—C$_6$H$_2$—O— | —(CH$_2$)$_7$— | | |
| 274a | 2,4,6-(CH$_3$)—C$_6$H$_2$—O— | —(CH$_2$)$_7$— | | |
| 275a | 1-naphthyl-O— | —(CH$_2$)$_7$— | | |
| 276a | 2-naphthyl-O— | —(CH$_2$)$_7$— | | |

TABLE 2-continued

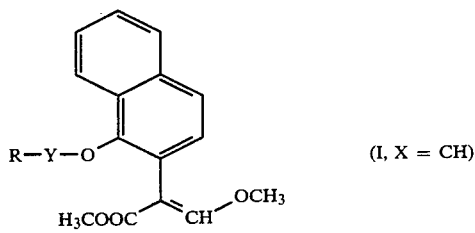

(I, X = CH)

| Comp. no. | R | Y | mp(°C.) | IR(cm$^{-1}$) |
|---|---|---|---|---|
| 277a | 4-($C_6H_5$—$CH_2$—O)$C_6H_4$—O— | —($CH_2$)$_7$— | | |
| 278a | $C_6H_5$—$CH_2$—O— | —($CH_2$)$_7$— | | |
| 279a | $C_6H_5$—O— | —($CH_2$)$_8$— | | |
| 280a | 2-Cl—$C_6H_4$—O— | —($CH_2$)$_8$— | | |
| 281a | 3-Cl—$C_6H_4$—O— | —($CH_2$)$_8$— | | |
| 282a | 4-Cl—$C_6H_4$—O— | —($CH_2$)$_8$— | | |
| 283a | 2-F—$C_6H_4$—O— | —($CH_2$)$_8$— | | |
| 284a | 3-F—$C_6H_4$—O— | —($CH_2$)$_8$— | | |
| 285a | 4-F—$C_6H_4$—O— | —($CH_2$)$_8$— | | |
| 286a | 2-$CH_3$—$C_6H_4$—O— | —($CH_2$)$_8$— | | |
| 287a | 3-$CH_3$—$C_6H_4$—O— | —($CH_2$)$_8$— | | |
| 288a | 4-$CH_3$—$C_6H_4$—O— | —($CH_2$)$_8$— | | |
| 289a | 2-$CH_3O$—$C_6H_4$—O— | —($CH_2$)$_8$— | | |
| 290a | 3-$CH_3O$—$C_6H_4$—O— | —($CH_2$)$_8$— | | |
| 291a | 4-$CH_3O$—$C_6H_4$—O— | —($CH_2$)$_8$— | | |
| 292a | 4-t-$C_4H_9$—$C_6H_4$—O— | —($CH_2$)$_8$— | | |
| 293a | 4-$C_2H_5O$—$C_6H_4$—O— | —($CH_2$)$_8$— | | |
| 294a | 4-$CF_3$—$C_6H_4$—O— | —($CH_2$)$_8$— | | |
| 295a | 4-$C_6H_5$—$C_6H_4$—O— | —($CH_2$)$_8$— | | |
| 296a | 4-($C_6H_5$—$CH_2$—O)—$C_6H_4$—O— | —($CH_2$)$_8$— | | |
| 297a | 2,4,6-$Cl_3$—$C_6H_2$—O— | —($CH_2$)$_8$— | | |
| 298a | 2,4,6-($CH_3$)$_3$—$C_6H_2$—O— | —($CH_2$)$_8$— | | |
| 299a | 1-naphthyl-O— | —($CH_2$)$_8$— | | |
| 300a | 2-naphthyl-O— | —($CH_2$)$_8$— | | |
| 301a | $C_6H_5$—$CH_2$—O— | —($CH_2$)$_8$— | | |
| 302a | $C_6H_5$—O— | —($CH_2$)$_9$— | | |
| 303a | $C_6H_5$—O— | —($CH_2$)$_{10}$— | | |
| 304a | 2-Cl—$C_6H_4$—O— | —($CH_2$)$_{10}$— | | |
| 305a | 3-Cl—$C_6H_4$—O— | —($CH_2$)$_{10}$— | | |
| 306a | 4-Cl—$C_6H_4$—O— | —($CH_2$)$_{10}$— | | |
| 307a | 2-F—$C_6H_4$—O— | —($CH_2$)$_{10}$— | | |
| 308a | 3-F—$C_6H_4$—O— | —($CH_2$)$_{10}$— | | |
| 309a | 4-F—$C_6H_4$—O— | —($CH_2$)$_{10}$— | | |
| 310a | 2-$CH_3$—$C_6H_4$—O— | —($CH_2$)$_{10}$— | | |
| 311a | 3-$CH_3$—$C_6H_4$—O— | —($CH_2$)$_{10}$— | | |
| 312a | 4-$CH_3$—$C_6H_4$—O— | —($CH_2$)$_{10}$— | | |
| 313a | 2-$CH_3O$—$C_6H_4$—O— | —($CH_2$)$_{10}$— | | |
| 314a | 3-$CH_3O$—$C_6H_4$—O— | —($CH_2$)$_{10}$— | | |
| 315a | 4-$CH_3O$—$C_6H_4$—O— | —($CH_2$)$_{10}$— | | |
| 316a | 4-t-$C_4H_9$—$C_6H_4$—O— | —($CH_2$)$_{10}$— | | |
| 317a | 4-$C_2H_5O$—$C_6H_4$—O— | —($CH_2$)$_{10}$— | | |
| 318a | 4-$CF_3$—$C_6H_4$—O— | —($CH_2$)$_{10}$— | | |
| 319a | 4-$C_6H_5$—$C_6H_4$—O— | —($CH_2$)$_{10}$— | | |
| 320a | 4-($C_6H_5$—$CH_2$—O)—$C_6H_4$—O— | —($CH_2$)$_{10}$— | | |
| 321a | 2,4,6-$Cl_3$—$C_6H_2$—O— | —($CH_2$)$_{10}$— | | |
| 322a | 2,4,6-($CH_3$)$_3$—$C_6H_2$—O— | —($CH_2$)$_{10}$— | | |
| 323a | 1-naphthyl-O— | —($CH_2$)$_{10}$— | | |
| 324a | 2-naphthyl-O— | —($CH_2$)$_{10}$— | | |
| 325a | $C_6H_5$—$CH_2$—O— | —($CH_2$)$_{10}$— | | |

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia species in cotton and lawns,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,

*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, for example against Paecilomyces variotii.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 2 is mixed with 10 parts by weight of N-methyl-α-pyrrolidone. A mixture is obtained which is suitable for application in the form of very fine drops.

II. 20 parts by weight of compound no. 3 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 4 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 6 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 13 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 19 is intimately mixed with 97 parts by weight of particulate kaolin. A dust is obtained containing 3% by weight of the active ingredient.

VII. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 3 is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 4 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

USE EXAMPLES

For comparison purposes, methyl 2-benzyloxyphenylglyoxylate O-methyloxime (A) disclosed in EP 253,213 was used.

USE EXAMPLE 1

Action on *Botrytis Cinerea* in Pimientos

Pimiento seedlings of the "Neusiedler Ideal Elite" variety with 4 to 5 well developed leaves were sprayed to runoff with aqueous suspensions containing (dry basis) 80% of active ingredient and 20% of emulsifier. After the sprayed-on layer had dried, the plants were sprayed with a conidial suspension of the fungus *Botrytis cinerea* and kept in a high-humidity chamber at 22° to 24° C. After 5 days, the disease had spread on the untreated control plants to such an extent that the necroses covered the major portion of the leaves.

The results show that active ingredients 6 and 13, applied as 0.05 wt % spray liquors, have a better fungicidal action (90%) than prior art active ingredient A (65%).

USE EXAMPLE 2

Action on *Pyrenophora Teres*

Barley seedlings of the "Igri" variety were sprayed to runoff at the two-leaf stage with aqueous suspensions consisting (dry basis) of 80% of active ingredient and 20% of emulsifier. After 24 hours the plants were inoculated with a spore suspension of the fungus *Pyrenophora teres*, and set up for 48 hours in a high-humidity climatic cabinet at 18° C. The plants were then cultivated for a further 5 days in the greenhouse at 20° to 22° C. and a relative humidity of 70° C. The extent of fungus spread was then assessed.

The results show that active ingredients 2, 3, 4, 6, 13 and 19, applied as 0.05 wt % spray liquors, have a better fungicidal action (90%) than prior art active ingredient A (60%).

We claim:

1. Ortho-substituted 1-naphthyl ethers of the general formula I

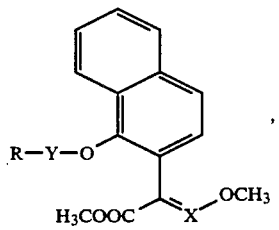

(I)

where X is N, Y is saturated or unsaturated $C_1$-$C_{12}$-alkylene and R is aryl, aryloxy, arylthio or arylalkoxy, it being possible for the aromatic ring to be substituted one to five times by the following: halogen, $C_1$-$C_6$-alkyl, $C_1$-$C_6$-alkoxy, $C_1$-$C_4$-alkylthio, $C_1$-$C_2$-haloalkyl, aryl, aryl-$C_1$-$C_2$-alkoxy, $C_1$-$C_4$-alkylcarbonyl, amino which is substituted once or twice by $C_1$-$C_4$-alkyl, or is cyano or nitro.

2. A process for combating fungi, wherein the fungi or the materials, plants, seed or soil threatened by fungus attack are treated with a fungicidally effective amount of a compound of the formula I

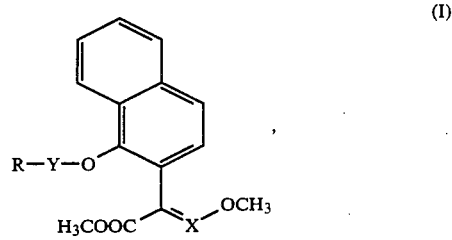

(I)

where X is N, Y is saturated or unsaturated $C_1$-$C_{12}$-alkylene and R is aryl, aryloxy, arylthio or arylalkoxy, it being possible for the aromatic ring to be substituted one to five times by the following: halogen, $C_1$-$C_6$-alkyl, $C_1$-$C_6$-alkoxy, $C_1$-$C_4$-alkylthio, $C_1$-$C_2$-haloalkyl, aryl, aryl-$C_1$-$C_2$-alkoxy, $C_1$-$C_4$-alkylcarbonyl, amino which is substituted once or twice by $C_1$-$C_4$-alkyl, or is cyano or nitro.

3. A fungicide containing an inert carrier and a fungicidally effective amount of a compound of the formula I

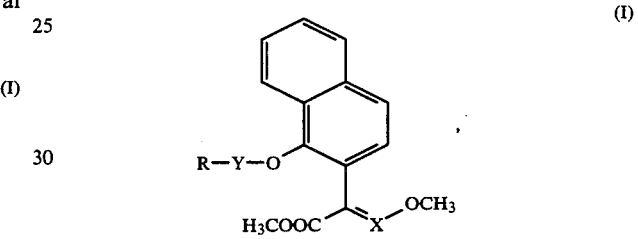

(I)

where X is N, Y is saturated or unsaturated $C_1$-$C_{12}$-alkylene and R is aryl, aryloxy, arylthio or arylalkoxy, it being possible for the aromatic ring to be substituted one to five times by the following: halogen, $C_1$-$C_6$-alkyl, $C_1$-$C_6$-alkoxy, $C_1$-$C_4$-alkylthio, $C_1$-$C_2$-haloalkyl, aryl, aryl-$C_1$-$C_2$-alkoxy, $C_1$-$C_4$-alkylcarbonyl, amino which is substituted once or twice by $C_1$-$C_4$-alkyl, or is cyano or nitro.

4. A compound of the formula I as set forth in claim 1, where R is 2-fluorophenyl, Y is $CH_2$ and X is N.

5. A compound of the formula I as set forth in claim 1, where R is 2-chlorophenyl Y is $CH_2$ and X is N.

6. A compound of the formula I as set forth in claim 1, where R is 2-bromophenyl, Y is $CH_2$ and X is N.

* * * * *